United States Patent [19]
Iyer et al.

[11] Patent Number: 5,614,622
[45] Date of Patent: Mar. 25, 1997

[54] 5-PENTENOYL MOIETY AS A NUCLEOSIDE-AMINO PROTECTING GROUP, 4-PENTENOYL-PROTECTED NUCLEOTIDE SYNTHONS, AND RELATED OLIGONUCLEOTIDE SYNTHESES

[75] Inventors: Radhakrishnan P. Iyer, Shrewsbury; Theresa Devlin, Jamaica Plain; Ivan Habus, Shrewsbury; Dong Yu, Shrewsbury; Sudhir Agrawal, Shrewsbury, all of Mass.

[73] Assignee: Hybridon, Inc., Worcester, Mass.

[21] Appl. No.: 518,921

[22] Filed: Aug. 24, 1995

Related U.S. Application Data

[63] Continuation-in-part of Ser. No. 457,198, Jun. 1, 1995.

[51] Int. Cl.$^6$ .......................... C07H 19/06; C07H 19/10; C07H 19/16; C07H 19/20; C07H 21/00
[52] U.S. Cl. .................................. 536/25.33; 536/25.34; 536/26.7; 536/26.71; 536/26.8; 536/27.62; 536/27.81; 536/28.51
[58] Field of Search .............................. 536/25.33, 25.34, 536/26.7, 26.74, 26.8, 26.9

[56] References Cited

U.S. PATENT DOCUMENTS 4,415,732  11/1983  Caruthers et al. .................... 536/25.34
5,149,798  9/1992  Agrawal et al. ........................ 536/25.3

OTHER PUBLICATIONS

Goodchild, "Conjugates of Oligonucleotides and Modified Oligonucleotides: A Review of Their Synthesis and Properties," *Bioconjugate Chemistry*, 1(3), 165–186 (1990); see p. 166, Scheme 1.
Sonveaux, "The Organic Chemistry Underlying DNA Synthesis," *Bioorganic Chemistry*, 14, 274–325 (1986).
*Aldrich Catalog/Handbook of Fine Chemicals*, 1984–85, Aldrich Chemical Co., Milwaukee, WI, 1984, see p. 858, 6th entry.
Oh et al., "Effect of Retinoyladenine (a Retinoid) on the Differentiation of HL–60 Cell," *Korean J. Biochem.*, 26(1), 39–45 (1994).
Iyer et al., "Methyl Phosphotriester Oligonucleotides: Facile Synthesis Using N–Pent–4–enoyl Nucleoside Phosphoramidites," *J. Organic Chem.*, 60(25, 8132–8133 (1995).
S. Agrawal, Ed., "Methods in Molecular Biology, vol. 20: Protocols for Oligonucleotides and Analogs", pp. 165–189, Humana Press, 1993.
F. Eckstein, Ed., "Oligonucleotides and Analogues: A Practical Approach", pp. 87–108, (1991).
Uhlmann and Peyman, Chem. Rev. 90:543 (1990).
Agrawal and Iyer, "Curr. Op. in Biotech. 6", 12–19 (1995).
Khorana et al., "J. Molec. Biol. 72", 209 (1972).
Beaucage and Caruthers, "Tetrahedron Lett. 22", 1859–1862 (1981).
Agrawal and Goodchild, "Tetrahedron Lett. 28", 3539–3542 (1987).
Connolly et al., "Biochemistry 23", 3443–3453 (1984).
Jager et al., "Biochemistry 27", 7237–7246 (1988).
Agrawal et al., "Proc. Natl. Acad. Sci. USA 85", 7079–7083 (1988).
Ravikumar et al., "Tetrahedron 50", 9255 (1994).
Iyer et al., "Nucleosides & Nucleotides 14", 1349–1357 (1995).
Kuijpers et al., "Nucl. Acids Res. 18", 5197–5205 (1990).
Reddy et al., "Tetrahedron Lett., 35", 5771–5774 (1994).

*Primary Examiner*—John Kight
*Assistant Examiner*—L. Eric Crane
*Attorney, Agent, or Firm*—Hale and Dorr

[57] ABSTRACT

The invention provides new methods for synthesizing oligonucleotides that allow for deprotection of the oligonucleotide under more mild conditions than existing methods. The invention further provides a nucleoside base protective group that is stable under oligonucleotide synthesis conditions, but which can be removed under more mild conditions than existing protective groups, as well as nucleoside synthons having such base protective groups.

5 Claims, No Drawings

5-PENTENOYL MOIETY AS A NUCLEOSIDE-AMINO PROTECTING GROUP, 4-PENTENOYL-PROTECTED NUCLEOTIDE SYNTHONS, AND RELATED OLIGONUCLEOTIDE SYNTHESES

This is a continuation-in-part of U.S. Ser. No. 08/457,198, filed 1 Jun. 1995.

BACKGROUND OF THE INVENTION

1. Field of the Invention

The invention relates to the chemical synthesis of oligonucleotides and to chemical entities useful in such synthesis.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g.,*Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6, 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron Lett.* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22, 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), teaches synthesis of oligonucleotide methylphosphonates using phosphoramidite chemistry. Connolly et al., *Biochemistry* 23, 3443 (1984), discloses synthesis of oligonucleotide phosphorothioates using phosphoramidite chemistry. Jager el al., *Biochemistry* 27, 7237 (1988), discloses synthesis of oligonucleotide phosphoramidates using phosphoramidite chemistry. Agrawal et al., *Proc. Antl. Acad. Sci. USA* 85, 7079–7083 (1988), discloses synthesis of oligonucleotide phosphoramidates and phosphorothioates using H-phosphonate chemistry.

Solid phase synthesis of oligonucleotides by each of the foregoing methods involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group of the incoming nucleoside and the 5' hydroxyl group of the 5'-most nucleoside of the nascent, support-bound oligonucleotide.

Refinement of methodologies is still required, however, particularly when making a transition to large-scale synthesis (10umol to 1 mmol and higher). See Padmapriya et al., *Antisense Res. Dev.* 4, 185 (1994). Several modifications of the standard phosphoramidite methods have already been reported to facilitate the synthesis (Padmapriya et al., supra; Ravikumar et al., *Tetrahedron* 50, 9255 (1994); Theisen et al., *Nucleosides & Nucleotides* 12, 43 (1994); and Iyer et al., *Nucleosides & Nucleotides* 14, 1349 (1995)) and isolation (Kuijpers et al. *Nucl. Acids Res.* 18, 5197 (1990); and Reddy et al., *Tetrahedron Lett.* 35, 4311 (1994)) of oligonucleotides.

The routine synthesis of oligonucleotides is presently carried out using various N-acyl protecting groups for the nucleoside bases, such as isobutyryl (for guanine), and benzoyl for adenine and cytosine. After the synthesis of the oligonucleotides is carried out using either phosphoramidite chemistry or H-phosphonate chemistry, the protecting groups are removed by treatment with ammonia at 55°–60° C. for 5–10 hours. Using these protecting groups, PO oligonucleotides and other modified oligonucleotides can be synthesized. But in certain instances where modified oligonucleotides are functionalized with base-sensitive groups, the functionalities often get removed while the deprotection is being carried out. Examples of such base-sensitive modified oligonucleotides include, ribonucleoside-containing oligonucleotides, methylphosphotriester oligonucleotides, phosphoramides, etc. In other applications of oligonucleotides, it is desirable to have oligonucleotides still bound to the solid support. Such completely deprotected oligonucleotides still bound to the solid support can be useful in a variety of applications such as those involving isolation of transcription factors and other factors or elements that interact with oligonucleotides. They are also useful for solid-phase PCR, investigation into nucleic acid protein interactions by, for example, NMR, creation and use of combinatorial libraries, screening of nucleic acid libraries, and solid support based hybridization probes (analogous to Southern and Northern blotting protocols). Creating such a support bound, deprotected oligonucleotide would be greatly aided by having a protective group that could be removed by mild conditions that would not cleave the oligonucleotide from the support.

There is, therefore, a need for methods for oligonucleotide synthesis that allow for deprotection of the oligonucleotide under more mild conditions than existing methods. There is further a need for nucleoside synthons having new base protective groups that are stable under oligonucleotide synthesis conditions, but which can be removed under more mild conditions than existing protective groups.

BRIEF SUMMARY OF THE INVENTION

The invention provides new methods for synthesizing oligonucleotides that allow for deprotection of the oligonucleotide under more mild conditions than existing methods. The invention further provides a nucleoside base protective group that is stable under oligonucleotide synthesis conditions, but which can be removed under more mild conditions than existing protective groups, as well as nucleoside synthons having such base protective groups.

In a first aspect, the invention provides a novel nucleoside base protective group having the general structure I:

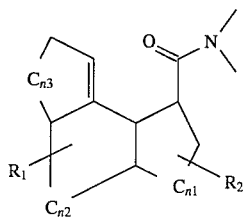

where $n_1$, $n_2$, $n_3$ are independently 0–10, the ring structures shown may be aromatic or heterocyclic, the nitrogen displayed is the protected amino moiety of the nucleoside base, and $R_1$ and $R_2$ are independently hydrogen, or an alkyl, aryl, aralkyl, ether, hydroxy, nitrile, nitro, ester, carboxyl, or aldehyde group. In a preferred embodiment, compound I has $n_1$, $n_2$ and $n_3$ values of 0, and thus takes the form N-pent-4-enoyl, i.e., $CH_2=CH(CH_2)_2CO$ —(II). Compounds I and II protect the nucleoside base amino moieties by forming amide linkages, as in:

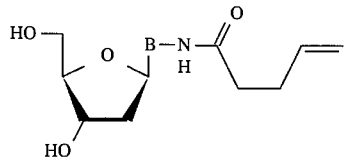

where the nitrogen displayed is the protected amino moiety of the base B.

Base protective group I and the preferred embodiment II are particularly advantageously used because they can be removed chemoselectively by treatment with a chemoselective removing agent. Thus, in a second aspect, the invention provides a method for synthesizing oligonucleotides that allows for removal of base protective groups under more mild conditions than existing methods. This new method comprises sequentially coupling nucleoside synthons having base protective groups according to the invention to produce a base-protected oligonucleotide, followed by deprotection using a chemoselective removing agent. The method according to the invention can utilize any known or otherwise suitable oligonucleotide synthesis chemistry, including the well known H-phosphonate and phosphoramidite chemistries.

The use of this new method provides numerous advantages. For example the method's mild procedure for removing the protective group without affecting the integrity of other functionalities present in the oligonucleotide makes it possible to prepare novel analogs of oligonucleotides such as ribonucleoside-containing oligonucleotides, alkylphosphotriesters, certain base-sensitive phosphoramidate and other base-sensitive oligonucleotides. Besides being able to synthesize oligonucleotides bearing "sensitive" functionalities, it can also be used in the routine synthesis of various oligonucleotides as in case of the conventional protecting groups. In addition, this new method allows for synthesis of oligonucleotides still bound to any type of solid support. Where an unprotected, support-bound oligonucleotide is desired, the full length support-bound oligonucleotide can have its internucleoside linkages oxidized, followed by contacting the oligonucleotide with a chemoselective removing agent to cleave the base protective group.

DETAILED DESCRIPTION OF THE PREFERRED EMBODIMENTS

The invention relates to the chemical synthesis of oligonucleotides and to chemical entities useful in such synthesis. The patents and publications identified in this specification are within the knowledge of those skilled in this field and are hereby incorporated by reference in their entirety.

The invention provides new methods for synthesizing oligonucleotides that allow for deprotection of the oligonucleotide under more mild conditions than existing methods. The invention further provides a nucleoside base protective group that is stable under oligonucleotide synthesis conditions, but which can be removed under more mild conditions than existing protective groups, as well as nucleoside synthons having such base protective groups.

In one aspect of the present invention, a novel nucleoside base protective group is provided. This protecting group has the general structure I:

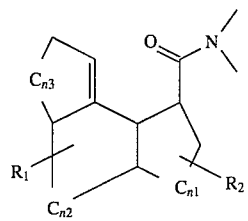

where $n_1$, n2, and $n_3$ are independently 0–10, the ring structures shown may be aromatic or heterocyclic, the nitrogen displayed is the protected amino moiety of the nucleoside base, and $R_1$ and $R_2$ are independently hydrogen, or an alkyl, aryl, aralkyl, ether, hydroxy, nitrile, nitro, ester, carboxyl, or aldehyde group.

In a preferred embodiment, compound I has $n_1$, $n_2$ and $n_3$ values of 0 and thus takes the form N-pent-4-enoyl, i.e., $CH_2=CH(CH_2)_2CO$—(II). Compounds I and II protect the nucleoside base amino moieties by forming amide linkages, as in:

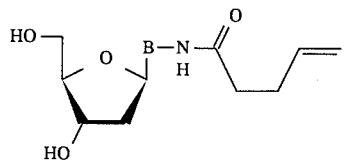

where the nitrogen displayed is the protected amino moiety of the nucleoside base B.

Base protective group I and the preferred embodiment II are particularly advantageously used because they can be removed chemoselectively by treatment with a chemoselective removing agent. Thus, in a second aspect, the invention provides a method for synthesizing oligonucleotides that allows for removal of base protective groups under more mild conditions than existing methods. In this method, nucleoside synthons having base protective groups according to the invention are sequentially coupled according to standard procedures to yield a base-protected oligonucleotide. The base-protective groups are then removed by a chemoselective removing agent. For purposes of the invention, a nucleoside synthon means a monomeric or multimeric nucleoside derivative appropriate for synthesis of an oligonucleotide. Preferred nucleoside synthons include monomeric nucleoside phosphoramidites, phosphotriesters, or H-phosphonates having a blocked 5'-OH, preferably blocked with a dimethoxytrityl group. A chemoselective removing agent means an agent that is capable of removing a base protective group according to the invention. In certain preferred embodiments, the chemoselective removing agent is selected from the group consisting of halogens, especially $Br_2$, $Cl_2$ and $I_2$, any of which are preferably taken up in water, or in pyridine/ROH, wherein R is an alkyl, aralkyl or aryl group having 1–10 carbon atoms, or as an N-halosuccinimide. In alternative embodiments, non-chemoselective reagents may be used, such as aqueous ammonium hydroxide, alcoholic ammonia, alkali carbonates in organic solvents, primary or secondary amines, alkali hydroxides, or any amidolytic reagent.

This method can utilize any suitable oligonucleotide synthesis chemistry, including the well known H-phosphonate and phosphoramidite chemistries. In one preferred embodiment, synthesis is carried out on a suitable solid support using either H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)). Synthesis on such a solid support begins with coupling a nucleoside synthon according to the invention to a nucleoside that is covalently linked the solid support (i.e., linked to a functionality on the solid support, preferably an amino or hydroxyl functionality). More generally, the method according to the invention can be used with any of the chemistries commonly used for oligonucleotide synthesis, whether in solution phase or in solid phase. Thus, the invention provides a method for synthesizing an oligonucleotide, the method comprising coupling suitable nucleoside synthon, such as a nucleoside H-phosphonate, a nucleoside phosphoramidite, or a nucleoside phosphotriester to a nucleoside and deprotecting a nucleoside base with a reagent comprising a halogen in water, or in pyridine/ROH, wherein R is an alkyl, aralkyl or aryl group having 1–10 carbon atoms. The nucleoside to which the nucleoside synthon is coupled may be a monomer, or it may be the terminal nucleoside of a growing oligonucleotide chain. In either case, the nucleoside or growing oligonucleotide chain may be support-bound or free in solution.

The versatility of chemical synthetic approach of the method according to the invention makes the method according to the invention suitable for the synthesis of any of a broad class of compounds, all of which are referred to herein as "oligonucleotides". For purposes of the invention, the term oligonucleotide includes polymers of two or more deoxyribonucleotide, or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O—lower alkyl group containing 1–6 saturated or unsaturated carbon atoms, or with an —O—aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

The use of this new method provides numerous advantages. For example the method's chemoselective capacity for removing the protective group without affecting the integrity of other functionalities present in the oligonucleotide makes it possible to prepare novel analogs of oligonucleotides such as oligoribonucleotides, alkylphosphotriesters, certain base sensitive phosphoramidate and other base-sensitive oligonucleotides. Besides being able to synthesize oligonucleotides bearing "sensitive" functionalities, it can also be used in the routine synthesis of various oligonucleotides as in case of the conventional protecting groups. In addition, this new method allows for synthesis of oligonucleotides still bound to any type of solid support. Where an unprotected, support-bound oligonucleotide is desired, the full length support-bound oligonucleotide will have its internucleoside linkages oxidized, followed by contacting the oligonucleotide with a chemoselective removing agent to cleave the base protective group. In the phosphoramidite approach, this is followed by treatment with anhydrous triethylamine to cleave the beta-cyanoethyl moiety.

Additionally, according to this aspect of the invention, support-bound branched oligonucleotides can be synthesized using, for example glycol residues in which one hydroxyl group is protected by e.g., DMT, and the other by a protecting group according to the invention. Then the DMT group may be selectively removed and an oligonucleotide synthesized from the resulting unprotected hydroxyl. Upon completion of that oligonucleotide, the hydroxyl moiety protected by the protecting group according to the invention can be deprotected with a chemoselective removing agent and another, different oligonucleotide synthesized from it.

The following examples further illustrate certain preferred embodiments of the invention and are not limiting in nature.

EXAMPLE 1

Preparation of N-Dent-4-enoyl 2'-deoxy adenosine (dA Npr):

2'-Deoxyadenosine (Mallinkckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4g, 20 mmol) was added and the contents stirred. After 15 min triethyl amine (3 ml) was added and the contents stirred for 2–3 h. The reaction slurry was cooled to 0°–5° C. and 10 ml of water was added. After 5 min., 28% $NH_4OH$ (10ml) was added. The resulting clear solution was evaporated to dryness. Water (150 ml) was added and the reaction mixture was extracted with ethylacetate: ether (50 ml, 1:1). The aqueous layer was separated and concentrated to a small volume. Upon leaving at room temperature, a white precipitate of the title compound was obtained. Filtration and drying gave ca. 3.5 g of pure title compound. Several experiments repeating the above procedure, using larger scale of operation, gave the title compound in 85–90% yield.

The same general procedure can be employed for the preparation of dG and dC protected nucleosides.

EXAMPLE 2

Preparation of 5'-O-DMT-N-4-pent-4-enoyl-nucleoside synthons

The title compound was prepared by adopting a procedure as described by Froehler in Protocols for Oligonucleotides and analogs, Agrawal, S. Ed., pp. 63–80 as given below:

To 544 mg (1.63 mmol) of dA(N-pr) in 20 ml of anhydrous pyridine was added 1,108 g (3.3 mmol) of dimethoxytritylchloride. The reaction mixture was stirred at room temperature for 12 h. The reaction mixture was evaporated to dryness. The residue was chromatographed over silica gel 60 and eluted with $CH_2C_{12}:CH_3OH:(Et)3N$ to give 0.73 of 5'-O-DMT-N-4-pent-4-enoyl-2'-deoxyadenosine as a white foamy material.

To a stirred solution of 1,2,4 triazole (0.944 g, 13.3 mmol) and triethylamine (5.5 ml, 30 mmol) in anhydrous $CH_2Cl_{12}$ (40 ml) was added $PCl_3$ (0.35 ml, 3.9 mmol) at room temperature under argon. After 30 min, the reaction mixture was cooled to 0° C. and 5'-DMT-protected nucleoside (500 mg, 0.88 mmol) in 15 ml $CH_2Cl_2$ was added dropwise over 10–15 min at 0° C. and allowed to warm to room temperature. The reaction mixture was poured into 1M triethylammoniumbicarbonate (TEAB) (75 ml, pH 8.5) with stirring. The mixture was transferred to a separatory funnel and the phases separated. The aqueous phase was extracted with methylene chloride and the combined organic phase washed with 1M TEAB (1×50 ml). The organic layer was dried over sodium sulfate and evaporated to dryness. The solid product thus obtained was purified by chromatography over silica gel. Elution with $CH_2Cl_2:CH_3OH:(Et)_3N$ (18:1:1) gave 0,065 g of the title compound.

Other H-phosphonate nucleosides are similarly prepared in overall yields ranging from 70–90%.

Similarly nucleoside 5'-O-DMT-3'-6-cyanoethyl-N,N-diisopropylphosphoramidites and 5'+O-DMT-3'-N-N-diisopropylphosphoramidites were prepared using standard protocols as described by Beaucage, S. L., in Protocols for Oligonucleotides and Analogs, Agrawal, S., Ed., pp. 33–61.

EXAMPLE 3

Solid phase coupling of nucleoside synthons and removal of base protective groups Nucleoside synthons prepared according to Example 2 were coupled using solid phase H-phosphonate methodology (Froehler ref. above). The support bound oligonucleotide H-phosphonate was then treated with a solution of 2% $I_2$ in (pyridine:water, 98:2) for 30 min. This procedure completely removes the base protecting groups. An additional step to oxidize the H-phosphonate internucleoside linkages is not necessary if one is making oligonucleotide phosphodiesters using H-phosphonate methodology because simultaneous oxidation and deprotection can be achieved in a single reaction using the $I_2$ reagent specified above. Otherwise, conversion of the internucleoside linkage to phosphorothioates, morpholidates, or alkyltriesters is carried out according to standard procedures.

What is claimed is:

1. A nucleoside base protecting group attached to a nucleoside base, the protecting group having the structure

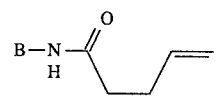

wherein B is a nucleoside base and the nitrogen displayed is the protected amino moiety of the nucleoside base.

2. A nucleoside synthon which is a nucleoside phosphoramidite, a nucleoside phosphotriester, or a nucleoside H-phosphonate having a base-protecting group according to claim 1.

3. A method for synthesizing an oligonucleotide, the method comprising coupling together two nucleoside synthons according to claim 2.

4. A method for synthesizing an oligonucleotide, the method comprising coupling a nucleoside synthon according to claim 2 to a nucleoside that is covalently bound to a suitable solid support.

5. A method for synthesizing an oligonucleotide, the method comprising coupling a nucleoside synthon according to claim 2 to a nucleoside and deprotecting the nucleoside base with a reagent comprising $Br_2$ or $I_2$ in water, or in pyridine/ROH, wherein R is an alkyl, aralkyl or aryl group having 1–10 carbon atoms.

* * * * *